United States Patent
Hess

(10) Patent No.: US 7,313,436 B2
(45) Date of Patent: Dec. 25, 2007

(54) CONFIGURABLE CARDIOVERSION AND DEFIBRILLATION THERAPIES IN THE PRESENCE OF COEXISTING ATRIAL AND VENTRICULAR ARRHYTHMIA

(75) Inventor: Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 539 days.

(21) Appl. No.: 10/426,495

(22) Filed: Apr. 30, 2003

(65) Prior Publication Data

US 2004/0220623 A1 Nov. 4, 2004

(51) Int. Cl.
*A61N 1/39* (2006.01)
(52) U.S. Cl. .................. 607/5; 607/9; 607/14
(58) Field of Classification Search .......... 607/4, 607/5, 9, 14
See application file for complete search history.

(56) References Cited

U.S. PATENT DOCUMENTS

| | | | |
|---|---|---|---|
| 4,316,472 A | 2/1982 | Mirowski et al. | |
| 4,375,817 A | 3/1983 | Engle et al. | |
| 4,384,585 A | 5/1983 | Zipes | |
| 4,577,633 A | 3/1986 | Berkovits et al. | |
| 4,587,970 A | 5/1986 | Holley et al. | |
| 4,726,380 A | 2/1988 | Vollmann et al. | |
| 4,727,877 A | 3/1988 | Kallok | |
| 4,800,883 A | 1/1989 | Winstrom | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |
| 5,107,850 A * | 4/1992 | Olive | 600/518 |
| 5,117,824 A | 6/1992 | Keimel et al. | |
| 5,163,427 A | 11/1992 | Keimel | |
| 5,188,105 A | 2/1993 | Keimel | |
| 5,261,400 A | 11/1993 | Bardy | |
| 5,411,524 A | 5/1995 | Rahul | |
| 5,439,481 A * | 8/1995 | Adams | 607/5 |
| 5,545,186 A | 8/1996 | Olson et al. | |
| 5,641,326 A * | 6/1997 | Adams | 607/5 |
| 6,091,988 A | 7/2000 | Warman et al. | |
| 6,178,350 B1 * | 1/2001 | Olson et al. | 607/4 |
| 6,442,425 B1 | 8/2002 | Alt | 607/4 |
| 6,721,597 B1 | 4/2004 | Bardy et al. | 607/4 |
| 2002/0143370 A1 | 10/2002 | Kim | 607/14 |

FOREIGN PATENT DOCUMENTS

EP 0 360 412 B1 3/1995
WO WO 92/18198 A2 10/1992

OTHER PUBLICATIONS

Steinhaus, David M et al. "Internal Defibrillation: Pain Perception of Low Energy Shocks", *Journal of Pacing and Clinical Electrophysiology*. vol. 25; (7) 2002:pp. 1090-1093
Stein KM et al "Simultaneous Atrial and Ventricular Tachyarrhythmias in Defibrillator Recipients: Does AF beget VF?" *J Am Coll Cardiol Proceedings*. 1999: p. 115A.

* cited by examiner

*Primary Examiner*—Angela D. Sykes
*Assistant Examiner*—Michael Kahelin
(74) *Attorney, Agent, or Firm*—Michael C Soldner

(57) ABSTRACT

An implantable cardioverter defibrillator system and method are provided having configurable shock therapies selected based on an evaluation of the atrial rhythm status following a ventricular tachycardia or fibrillation detection. A dual chamber shock configuration is selected if the ventricular arrhythmia is co-existing with an atrial arrhythmia of recent onset. A ventricular only shock configuration is selected if the ventricular arrhythmia is co-existing with a sustained atrial arrhythmia.

22 Claims, 4 Drawing Sheets

CONFIGURABLE CARDIOVERSION AND DEFIBRILLATION THERAPIES IN THE PRESENCE OF COEXISTING ATRIAL AND VENTRICULAR ARRHYTHMIA

FIELD OF THE INVENTION

The present invention relates generally to the field of implantable medical devices and in particular to an implantable medical device and system capable of detecting and treating dual chamber cardiac arrhythmias.

BACKGROUND OF THE INVENTION

Implantable cardioverter defibrillators (ICDs) are capable of detecting cardiac arrhythmias and delivering electrical stimulation therapies to terminate the detected arrhythmias. Tachycardia may be terminated by anti-tachycardia pacing therapies or high-voltage cardioversion shocks. Fibrillation may be terminated by high-voltage defibrillation shocks. These high-voltage shocks, which are referred to inclusively herein as "cardioversion/defibrillation shocks," can be life-saving to a patient but can be very painful.

Atrial arrhythmias, such as atrial tachycardia (AT) and atrial fibrillation (AF), may not be directly life threatening and may occur repeatedly in some patients. Therefore, in order to avoid delivering frequent, painful shock therapies, atrial cardioversion/defibrillation therapies employing high-voltage shocks may be programmed to be disabled in an ICD or programmed to be delivered after the AT/AF episode has been detected for a sustained period of time, for example 2 hours or longer. Atrial arrhythmia detection algorithms may remain enabled because a physician may want to monitor for the presence of AT and AF for the purposes of managing medical therapies, such as anti-coagulation therapy and anti-arrhythmic drugs. Furthermore, non-painful, anti-tachycardia pacing therapies may be delivered in an attempt to terminate a detected atrial arrhythmia. If these less aggressive therapies fail, however, or if all atrial arrhythmia therapies are disabled, the atrial arrhythmia may be sustained for long periods of time.

A dual arrhythmia is the presence of ventricular fibrillation (VF) or ventricular tachycardia (VT) preceded by the onset of and co-existing with AF or AT. Retrospective analysis of arrhythmia incidence in patients implanted with the Medtronic Model 7250 dual chamber ICD revealed that atrial fibrillation (AF) is a co-existent arrhythmia with ventricular tachycardia (VT) or ventricular fibrillation (VF) in a significant patient population. Approximately 18% of all VF episodes and 3% of all VT episodes were accompanied by recent onset AF or AT. Stein KM et al., J Am Coll Cardiol Proc., 1999.

In modern ICDs, the delivery of cardioversion/defibrillation shocks can be programmed according to a number of delivery parameters such as the shock vector, the shock energy, shock waveform, shock pulse shape and the tilt. The electrodes selected from the implanted lead system associated with the ICD determine the shock vector. The tilt is the percentage by which the high-voltage output pulse decreases in amplitude before output is truncated. The shock waveform can be monophasic, biphasic, triphasic, etc., and the shock pulse shape may be ramped, square, etc.

Depending on these selected parameters, a cardioversion/defibrillation shock delivered to terminate VT/VF may also terminate AT or AF if present. There is some risk, however, in terminating AT or AF when the duration of the AT/AF episode and the anti-coagulation status of the patient are unknown. During sustained AT/AF episodes, blood stasis in the atria can result in the formation of clots or thrombus. If AT/AF is suddenly terminated, coordinated atrial contraction may dislodge the clot, producing thromboembolism and leading to a high risk of stroke. Conversely, conversion of recent onset AT/AF simultaneously with the ventricular arrhythmia treatment would be more desirable than converting just the ventricular fibrillation or tachycardia alone.

Currently, ICDs control arrhythmia therapy delivery based on the type of arrhythmia detected independent of the rhythm of the opposite chamber. Detection of ventricular arrhythmias generally takes precedence over the detection of atrial arrhythmias because of the more serious nature of ventricular arrhythmias. Reference is made, for example, to U.S. Pat. No. 5,545,186 issued to Olson et al., which generally discloses a prioritized rule-based algorithm for arrhythmia detection, incorporated herein by reference in its entirety. Such prioritized arrhythmia detection has important advantages in detecting and treating the most lethal forms of arrhythmias first. Once a ventricular arrhythmia has been diagnosed by review of both atrial and ventricular information, therapies are delivered for treatment of the ventricular arrhythmia independent of the atrial rhythm at the time.

From the above discussion, however, it is apparent that it is desirable to take into account the status of the atrial rhythm when selecting the configuration of ventricular cardioversion/defibrillation therapy. A need remains, therefore, for a method that allows the configuration of a cardioversion/defibrillation therapy delivered in response to ventricular arrhythmia detection to be selected based on the status of both the atrial and ventricular rhythms.

SUMMARY OF THE INVENTION

An implantable cardioverter defibrillator system and method are provided having configurable cardioversion/defibrillation therapies selected based on an evaluation of the atrial rhythm status at the time of ventricular tachycardia or fibrillation detection. The system includes an ICD and associated leads for sensing cardiac signals for detecting arrhythmias in both the atrial and ventricular heart chambers and for delivering high-voltage cardioversion/defibrillation therapies. The system may additionally provide bradycardia and/or anti-tachycardia pacing therapies. Control circuitry included in the ICD allows high-voltage cardioversion/defibrillation shocks to be selectively configured dependent on the presence of sustained or recent onset AT/AF at the time of VT or VF detection. Parameters controlling the cardioversion/defibrillation shock configuration may include, but are not limited to, the shock vector, shock energy, tilt, waveform and/or wave shape.

The method includes detecting ventricular tachycardia or fibrillation (VT/VF), and, if a high-voltage cardioversion/defibrillation therapy is required, determining if an atrial arrhythmia is present. If an atrial arrhythmia is present, the method further includes determining if the atrial arrhythmia episode is sustained or of recent onset based on the duration of the atrial detection episode. The method further includes selecting a dual chamber cardioversion/defibrillation therapy if the atrial arrhythmia is of recent onset and selecting a ventricular-only cardioversion/defibrillation therapy if the atrial arrhythmia is sustained. Uniquely programmable sequences of shock configurations may be provided for delivering dual chamber cardioversion/defibrillation and ventricular-only cardioversion/defibrillation. As with current ICDs, separate therapies are available for VT, fast ventricular tachycardias (FVT), and ventricular fibrillation (VF).

The system and method of the present invention advantageously provide dual chamber cardioversion/defibrillation in the presence of dual arrhythmias when the atrial arrhythmia is of recent onset. Moreover, the system and method of the present invention reduce the risk of thromboembolism by providing ventricular-only cardioversion/defibrillation in the presence of sustained atrial arrhythmias. Features of the present invention also allow for the incidence of dual arrhythmias to be documented, segregated by recent onset and sustained atrial arrhythmias.

DETAILED DESCRIPTION OF THE INVENTION

Dual chamber ICDs sense both atrial and ventricular events for the detection of arrhythmias in both chambers. The present invention takes advantage of the ability to monitor the duration of an atrial arrhythmia episode in a dual chamber ICD when automatically selecting ventricular shock therapy configurations in response to VT/VF detection. As such, the present invention is preferably embodied in a dual chamber or multichamber ICD, such as the ICD shown in FIG. 1.

Figure 1:
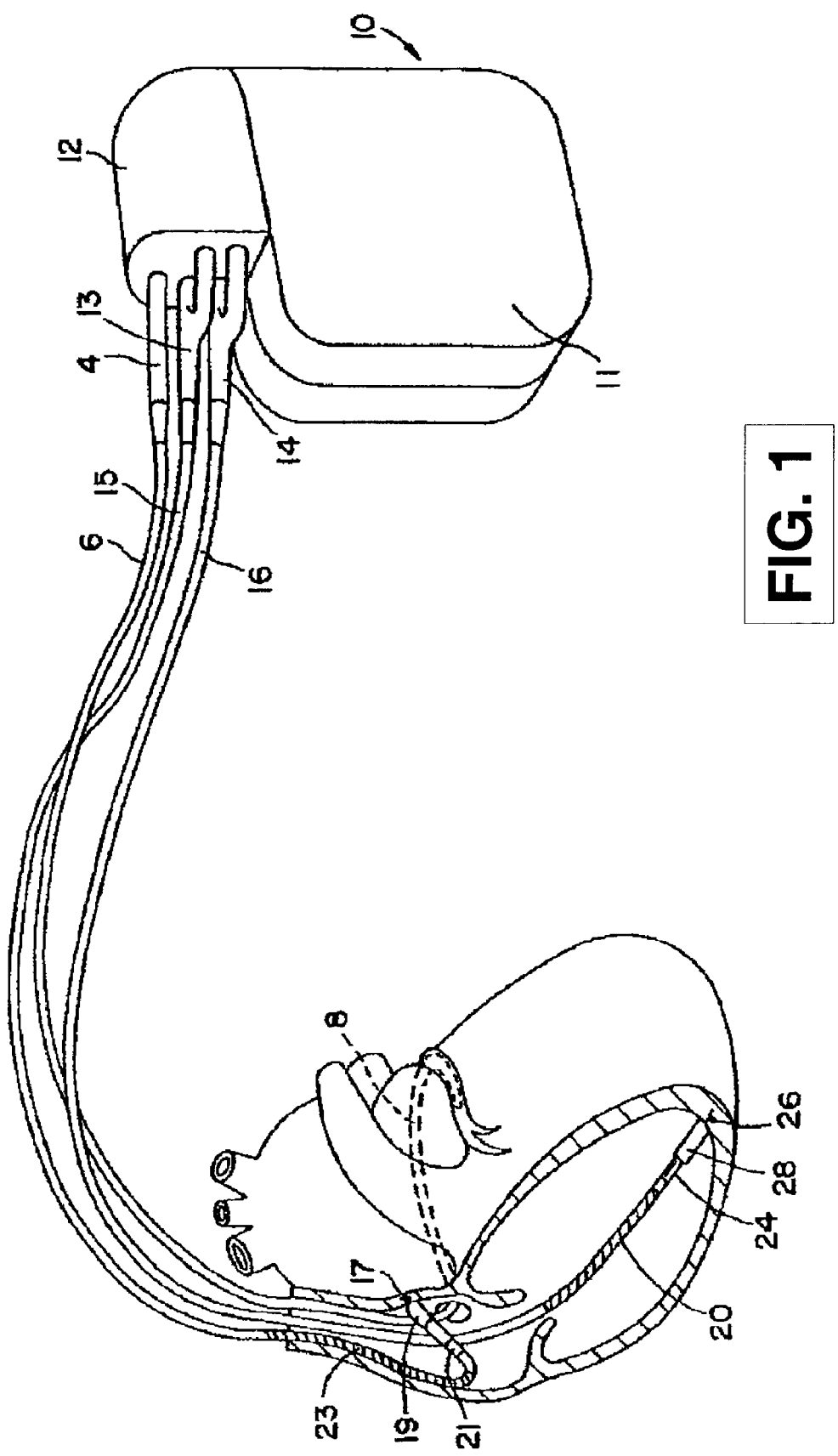
FIG. 1 is an illustration of an implantable pacemaker cardioverter defibrillator coupled to a patient's heart by way of three.

FIG. 1 is an illustration of an implantable pacemaker cardioverter defibrillator 10 coupled to a patient's heart by way of three leads 6, 15, and 16. A connector block 12 receives the proximal end of a right ventricular lead 16, a right atrial lead 15 and a coronary sinus lead 6, used for positioning electrodes for sensing and stimulation in three or four heart chambers. In FIG. 1, the right ventricular lead 16 is positioned such that its distal end is in the right ventricle (RV) for sensing right ventricular cardiac signals and delivering pacing or shocking pulses in the right ventricle. For these purposes, right ventricular lead 16 is equipped with a ring electrode 24, an extendable helix electrode 26 mounted retractably within an electrode head 28, and RV coil electrode 20, each of which are connected to an insulated conductor contained within the body of lead 16. The proximal end of the insulated conductors are coupled to corresponding connectors carried by bifurcated connector 14 at the proximal end of lead 16 for providing electrical connection to the ICD 10.

The right atrial lead 15 is positioned such that its distal end is in the vicinity of the right atrium and the superior vena cava (SVC). Lead 15 is equipped with a ring electrode 21 and an extendable helix electrode 17, mounted retractably within electrode head 19, for sensing and pacing in the right atrium. Lead 15 is further equipped with an SVC coil electrode 23 for delivering high-energy shock therapy. The ring electrode 21, the helix electrode 17 and the SVC coil electrode 23 are each connected to an insulated conductor within the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the RV coil electrode 20 or the SVC coil electrode 23 for delivering electrical shocks for cardioversion and defibrillation therapies. In other embodiments, coronary sinus lead 6 may also be equipped with a distal tip electrode and ring electrode for pacing and sensing functions in the left chambers of the heart. The coil electrode 8 is coupled to an insulated conductor within the body of lead 6, which provides connection to the proximal connector 4.

The electrodes 17 and 21 or 24 and 26 may be used as bipolar pairs, commonly referred to as a "tip-to-ring" configuration, or individually in a unipolar configuration with the device housing 11 serving as the indifferent electrode, commonly referred to as the "can" or "case" electrode. The device housing 11 may also serve as a subcutaneous defibrillation electrode in combination with one or more of the defibrillation coil electrodes 8, 20 or 23 for defibrillation of the atria or ventricles. It is recognized that alternate lead systems may be substituted for the three lead system illustrated in FIG. 1. While a particular multi-chamber ICD and lead system is illustrated in FIG. 1, methodologies included in the present invention may be adapted for use with other dual chamber, or multichamber ICD systems involving multiple electrodes for pacing/sensing and/or defibrillation within the heart or external to the heart such as epicardial or subcutaneous placements.

Figure 2:
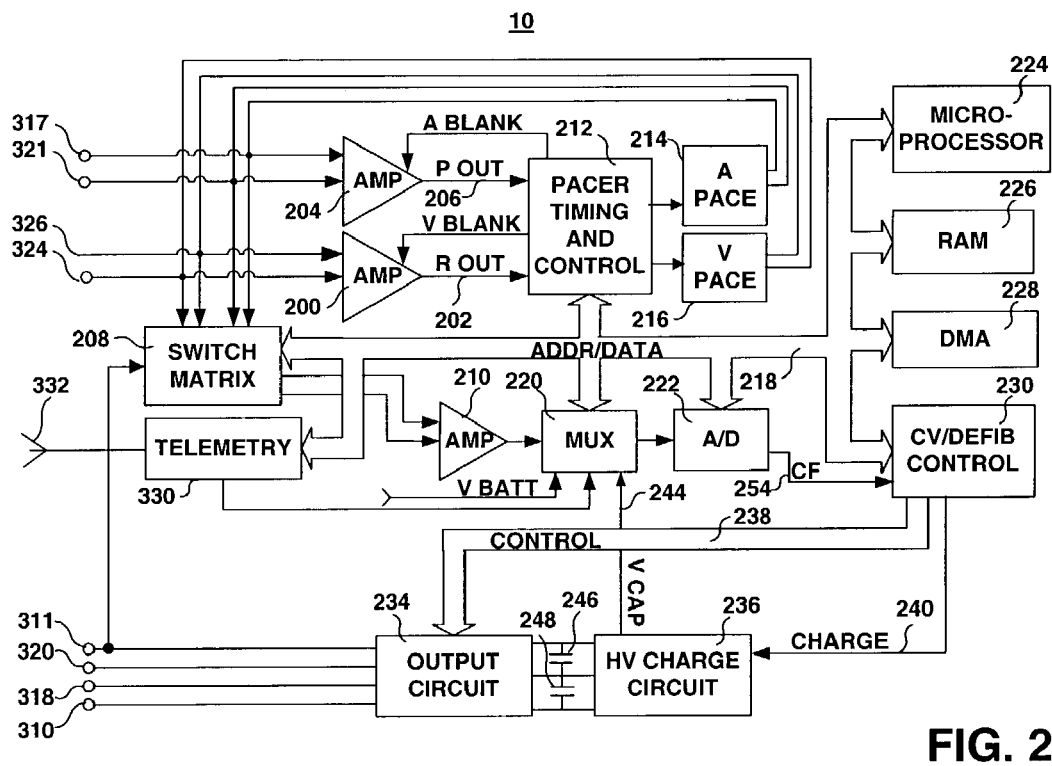
FIG. 2 is a functional block diagram of an ICD of FIG. 1 in which the present invention may usefully be practiced.

FIG. 2 is a functional block diagram of an ICD in which the present invention may usefully be practiced. This diagram should be taken as exemplary of the type of device with which the invention may be embodied and not as limiting, as it is believed that the invention may usefully be practiced in a wide variety of device implementations, including cardioverters and defibrillators which do not provide anti-tachycardia pacing therapies or do not include bradycardia pacing. The implementation may also include a device that does not employ pacing leads as described here to detect and treat arrhythmias. For example, a device implanted subcutaneously or sub-muscularly in a position over the heart such as an axillary location could use non-intracardiac lead based methods of electrical sensing to detect and deliver therapy. The disclosed embodiment shown in FIG. 2 is a microprocessor-controlled device, but the methods of the present invention may also be practiced with devices employing dedicated digital circuitry for controlling some device functions.

With regard to the electrode system illustrated in FIG. 1, the ICD 10 is provided with a number of connection terminals for achieving electrical connection to the cardiac leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11.

In accordance with the present invention, and as will be described in greater detail below, a shock vector may be selected from the available coil electrodes based on the status of both the atrial and ventricular rhythms.

The connection terminals 317 and 321 provide electrical connection to the helix electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the helix electrode 26 and the ring electrode 24 positioned in the right ventricle. The connection terminals 326 and 324 are further coupled to a ventricular sense amplifier 200 for sensing ventricular signals.

The atrial sense amplifier 204 and the ventricular sense amplifier 200 preferably take the form of automatic gain controlled amplifiers with adjustable sensing thresholds. The general operation of the ventricular sense amplifier 200 and the atrial sense amplifier 204 may correspond to that disclosed in U.S. Pat. No. 5,117,824, by Keimel, et al., incorporated herein by reference in its entirety. Whenever a signal received by atrial sense amplifier 204 exceeds an atrial sensing threshold, a signal is generated on the P-out signal line 206. Whenever a signal received by the ventricular sense amplifier 200 exceeds a ventricular sensing threshold, a signal is generated on the R-out signal line 202.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion and defibrillation functions of the ICD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal processing methods known in the art.

The telemetry circuit 330 receives downlink telemetry from and sends uplink telemetry to an external programmer, as is conventional in implantable anti-arrhythmia devices, by means of an antenna 332. Received telemetry is provided to microprocessor 224 via multiplexer 220. Data to be uplinked to the programmer and control signals for the telemetry circuit 330 are provided by microprocessor 224 via address/data bus 218. Data to be uplinked may include a record of detected arrhythmia episodes as is customary in modern ICDs. In accordance with the present invention, a record of detected VT/VF co-existing with AT/AF, referred to herein as "dual arrhythmias," may be segregated according to whether the atrial arrhythmia is a sustained episode or of recent-onset. Numerous types of telemetry systems known for use in implantable devices may be used.

The remainder of circuitry illustrated in FIG. 2 is dedicated to the provision of cardiac pacing, cardioversion and defibrillation therapies and, for the purposes of the present invention, may correspond to circuitry known in the prior art. In the exemplary embodiment shown in FIG. 2, the pacer timing and control circuitry 212 includes programmable digital counters which control the basic time intervals associated with various single, dual or multi-chamber pacing modes or anti-tachycardia pacing therapies delivered in the atria or ventricles. Pacer circuitry 212 also determines the amplitude of the cardiac pacing pulses under the control of microprocessor 224.

During pacing, escape interval counters within pacer timing and control circuitry 212 are reset upon sensing of R-waves or P-waves as indicated by signals on lines 202 and 206, respectively. In accordance with the selected mode of pacing, pacing pulses are generated by atrial pacer output circuit 214 and ventricular pacer output circuit 216. The pacer output circuits 214 and 216 are coupled to the desired electrodes for pacing via switch matrix 208. The escape interval counters are reset upon generation of pacing pulses, and thereby control the basic timing of cardiac pacing functions, including anti-tachycardia pacing.

The durations of the escape intervals are determined by microprocessor 224 via data/address bus 218. The value of the count present in the escape interval counters when reset by sensed R-waves or P-waves can be used to measure R-R intervals, P-P intervals, P-R intervals, and R-P intervals, which measures are stored in memory 226 and to diagnose the occurrence of a variety of arrhythmias.

Microprocessor 224 operates as an interrupt driven device and is responsive to interrupts from pacer timing and control circuitry 212 corresponding to the occurrences of sensed P-waves and R-waves and corresponding to the generation of cardiac pacing pulses. Any necessary mathematical calculations to be performed by microprocessor 224 and any updating of the values or intervals controlled by pacer timing/control circuitry 212 take place following such interrupts. A portion of the random access memory 226 may be configured as a number of recirculating buffers capable of holding a series of measured intervals, which may be analyzed in response to a pace or sense interrupt by microprocessor 224 for diagnosing an arrhythmia. A prioritized rule-based algorithm for classifying the heart rhythm as generally disclosed in the above-cited U.S. Pat. No. 5,545,186 issued to Olson et al., incorporated herein by reference in its entirety, and as currently implemented in commercially available Medtronic dual chamber implantable cardioverter defibrillators as PR Logic™, may be successfully employed for use with the present invention. However, any of the various arrhythmia detection methodologies known to the art may alternatively be employed.

In response to the detection of atrial or ventricular tachycardia, an anti-tachycardia pacing therapy may be delivered if desired by loading a regimen from microcontroller 224 into the pacer timing and control circuitry 212 according to the type of tachycardia detected. Alternatively, circuitry for controlling the timing and generation of anti-tachycardia pacing pulses as generally described in U.S. Pat. No. 4,577,633 issued to Berkovits et al., U.S. Pat. No. 4,880,005 issued to Pless et al., U.S. Pat. No. 4,726,380 issued to Vollmann et al., and U.S. Pat. No. 4,587,970 issued to Holley et al, all of which patents are incorporated herein by reference in their entireties, may be used.

In the event that higher voltage cardioversion or defibrillation shock pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors 246 and 248 is monitored via a voltage capacitor (VCAP) line 244, which is passed through the multiplexer 220. When the voltage reaches a predetermined value set by microprocessor 224, a logic signal is generated on the capacitor full (CF) line 254, terminating charging.

Thereafter, timing of the delivery of the defibrillation or cardioversion pulse is controlled by pacer timing and control circuitry 212.

An embodiment of an appropriate system for delivery and synchronization of ventricular cardioversion and defibrillation pulses and for controlling the timing function related to them is generally disclosed in commonly assigned U.S. Pat. No. 5,188,105 to Keimel, incorporated herein by reference in its entirety. If atrial defibrillation capabilities are included in the device, appropriate systems for delivery and synchronization of atrial cardioversion and defibrillation pulses and for controlling the timing function related to them may be found in U.S. Pat. No. 4,316,472 issued to Mirowski et al., U.S. Pat. No. 5,411,524 issued to Mehra, or U.S. Pat. No. 6,091,988 issued to Warman, all of which patents are incorporated herein by reference in their entireties. Any known ventricular cardioversion or defibrillation pulse control circuitry may be usable in conjunction with the present invention. For example, circuitry controlling the timing and generation of cardioversion and defibrillation pulses as disclosed in U.S. Pat. No. 4,384,585, issued to Zipes, U.S. Pat. No. 4,949,719, issued to Pless et al., and in U.S. Pat. No. 4,375,817, issued to Engle et al., all incorporated herein by reference in their entireties may be used in a device employing with the present invention.

In the illustrated device, delivery of cardioversion or defibrillation pulses is accomplished by output circuit 234, under control of control circuitry 230 via control bus 238. Output circuit 234 determines the shock pulse waveform, e.g. whether a monophasic, biphasic or multiphasic pulse is delivered, whether the housing 311 serves as cathode or anode, which electrodes are involved in delivery of the pulse, and the pulse shape and tilt. Examples of high-voltage cardioversion or defibrillation output circuitry are generally disclosed in U.S. Pat. No. 4,727,877 issued to Kallok, and U.S. Pat No. 5,163,427 issued to Keimel, both incorporated herein by reference in their entirety. In accordance with the present invention, the parameters controlling the high-voltage output in response to ventricular tachycardia or fibrillation detection are selected based on an evaluation of the atrial rhythm status as will be described in conjunction with FIG. 3.

Examples of output circuitry for delivery of biphasic pulse regimens may be found in U.S. Pat. No. 5,261,400 issued to Bardy, and U.S. Pat. No. 4,953,551 issued to Mehra et al., incorporated herein by reference in its entirety. An example of circuitry which may be used to control delivery of monophasic pulses is set forth in the above cited U.S. Pat. No. 5,163,427, to Keimel. However, output control circuitry for generating a multiphasic defibrillation pulse as generally disclosed in U.S. Pat. No. 4,800,883, issued to Winstrom, incorporated herein by reference in its entirety, may also be used in conjunction with a device embodying the present invention.

In modern implantable cardioverter defibrillators, the particular therapies are programmed into the device ahead of time by the physician, and a menu of therapies is typically provided. For example, on initial detection of tachycardia, an anti-tachycardia pacing therapy may be selected. On redetection of tachycardia, a more aggressive anti-tachycardia pacing therapy may be scheduled. If repeated attempts at anti-tachycardia pacing therapies fail, a higher-level cardioversion pulse therapy may be selected thereafter. As in the case of currently available ICDs, and as discussed in the above-cited references, it is envisioned that the amplitude of the defibrillation shock may be incremented in response to failure of an initial shock or shocks to terminate fibrillation. Prior art patents illustrating such pre-set therapy menus of anti-tachycardia therapies include the above-cited U.S. Pat. No. 4,726,380 issued to Vollmann et al., above cited U.S. Pat. No. 4,587,970 issued to Holley et al., and U.S. Pat. No. 4,830,006 issued to Haluska, incorporated herein by reference in their entirety.

Figure 3:
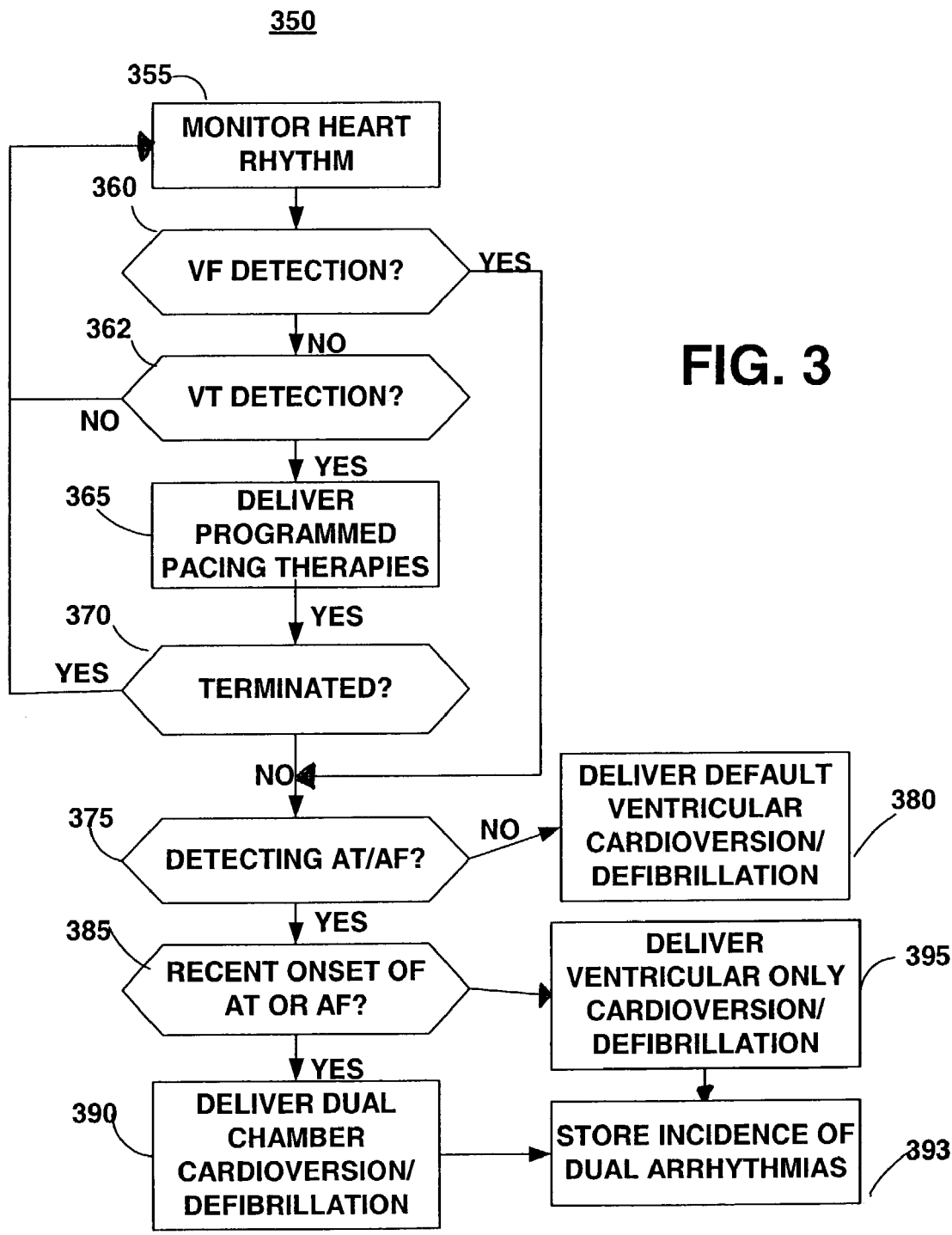
FIG. 3 is a flow chart summarizing the steps included in a method for configuring the delivery of a cardioversion/defibrillation therapy based on an evaluation of both the ventricular and atrial rhythms.

FIG. 3 is a flow chart of a method, according to the present invention, for configuring the delivery of a cardioversion/defibrillation therapy based on an evaluation of both the ventricular and atrial rhythms. According to the present invention, the heart rhythm is monitored by the ICD at step 355 according to the programmed atrial and ventricular arrhythmia detection algorithms. If VF is detected at decision step 360, method 350 skips directly to step 375. If VT is detected at decision step 362, any anti-tachycardia pacing therapies that are enabled, according to programmed tiered therapy regimes, are delivered at step 365 in an attempt to terminate a detected VT without delivering a painful, high-voltage shock. If the anti-tachycardia pacing therapies are successful, such that the ICD is no longer detecting VT at decision step 370, method 350 returns to step 355 to continue monitoring the heart rhythm.

If VT was detected at step 362 and either anti-tachycardia pacing therapies failed or were not enabled (such that the ICD is still detecting VT at decision step 370),or if VF was detected, the ICD will typically be programmed to deliver a high-voltage shock to treat the VT/VF. However, in accordance with the present invention, prior to delivering a cardioversion/defibrillation shock, the ICD will determine if an atrial arrhythmia is present at decision step 375. This determination may be made after VT/VF detection by means of a retrospective review of cardiac information, or the determination of an atrial arrhythmia may already have been made prior to VT/VF detection. Due to the time-critical nature of VT/VF delivery, delays to therapy while confirming atrial arrhythmias are preferably avoided by minimizing the time required to determine atrial rhythm status.

If no atrial arrhythmia is being detected, the ventricular cardioversion/defibrillation shock is delivered at step 380 according to "default" parameters, which have been programmed previously for VT or VF termination. If, however, the ICD is detecting AT or AF in addition to VT/VF, as determined at decision step 375, method 350 determines if the AT/AF episode is a sustained or recent onset episode at decision step 385. Typically, a recent onset AT or AF episode is an episode that has been continuously detected for less than 24 hours. A sustained episode of AT or AF is an episode that has been continuously detected for more than 24 hours. It is recognized that alternative time durations may be defined, and which may be programmable, for discriminating between recent onset and sustained atrial arrhythmias.

As noted previously, atrial arrhythmia detection algorithms may be enabled in some patients without enabling atrial therapies, or, in some cases, atrial anti-tachycardia pacing therapies may be enabled but not atrial shock therapies. Therefore, a sustained atrial arrhythmia may be present that has either been left untreated or been unsuccessfully treated by anti-tachycardia pacing. In other cases, an atrial arrhythmia may be of recent onset but the operating arrhythmia detection algorithms may give priority to the detection of the more serious VTNF, ignoring the presence of the AT/AF. However, in accordance with the present invention, the status of the atrium is evaluated before delivering a shock therapy in response to the VTNF detection such that the cardioversion/defibrillation shock may be configured to provide either "dual chamber" cardioversion/defibrillation or "ventricular only" cardioversion/defibrillation.

If detected AT/AF is determined to be of recent onset at decision step 385, a dual chamber cardioversion/defibrillation shock is delivered at step 390. A dual chamber cardioversion/defibrillation shock is delivered according to parameters that are likely to terminate both VT/VF and AT/AF. Parameters that may be adjusted to deliver this dual chamber cardioversion/defibrillation shock will typically include, but are not limited to, the shock vector, the shock energy, and/or the tilt. Other parameters that may additionally or alternatively be adjusted include the waveform, e.g, monophasic, biphasic, triphasic, etc., or waveshape, e.g. ramp, square pulse, etc.

For example, in order to cardiovert both the atria and the ventricles, a shock configuration that includes an RV coil, an SVC coil and the ICD can may be selected for delivering a shock having energy relatively greater than the shock energy for cardioverting only the ventricles. According to prior art, an initial ventricular cardioversion/defibrillation therapy is routinely programmed to energy levels of 10-12J to attempt to conserve battery energy and reduce the capacitor charge time to the initial therapy. This energy level is less likely to convert the atrium than a higher-energy shock. Prior study has demonstrated that patient perceived pain of shocks 2J and higher do not vary by shock energy. See Steinhaus DM, et al., PACE 2002. Therefore an initial shock of 30J could be delivered in a dual chamber cardioversion/defibrillation configuration to increase likelihood of AT/AF conversion at the same time as ventricular cardioversion/defibrillation. In this way, a single shock therapy may be delivered to treat both the AT/AF and VT/VF at the same time thus avoiding the need for two shock therapies for cardioverting/defibrillating the atria and ventricles separately.

If the AT or AF episode is determined to be a sustained episode at step 385, shock parameters are preferably configured for treating only the ventricles such that the risk of thromboembolism due to termination of the sustained AT/AF is avoided. At step 395, a "ventricular only" shock is delivered. Shock parameters that may be adjusted to deliver this "ventricular only" cardioversion/defibrillation may include, but are not limited to, the shock vector, the shock energy, tilt, shock waveform, and/or shock wave shape. For example, a shock configuration that includes only the RV coil and ICD can may be selected for delivering a shock energy that is relatively lower than the shock energy that would be selected for dual chamber cardioversion/defibrillation.

It is recognized that if an initial shock attempted for "ventricular only" cardioversion/defibrillation fails to terminate VT/VF, subsequent shocks may be needed in order to successfully terminate VT/VF. These subsequent shocks may also be configured to be "ventricular only" shocks, but shock configurations including higher energy shocks, alternative shock vectors, and/or different tilt, waveform and/or wave shape, may be needed in order to successfully terminate VT/VF. Thus, subsequent shock attempts may result in dual chamber cardioversion/defibrillation in order to terminate VT/VF, which is a more immediate life-threatening condition than the potential thromboembolic risk associated with terminating the sustained AT/AF.

Hence, in accordance with the present invention, shock therapy sequences may be uniquely programmed for responding to three different situations identified by analyzing the atrial rhythm status after a VT/VF detection is made: 1) a "default" ventricular cardioversion/defibrillation shock sequence for terminating a ventricular arrhythmia in the absence of any atrial arrhythmia, step 380, 2) a "dual chamber" cardioversion/defibrillation shock sequence for terminating a dual arrhythmia when VT/VF is co-existing with recent onset AT/AF, step 390, and 3) a "ventricular only" shock sequence for preferentially terminating the ventricular arrhythmia and leaving the atrial arrhythmia untreated when VTNF is co-existing with sustained AT/AF, step 395. In one embodiment, the default and dual chamber shock sequences may be provided as the same shock sequences. As with current ICDs, separate therapy sequences are available for VT, fast ventricular tachycardias (FVT), and ventricular fibrillation (VF). At step 393, the occurrence of the detected dual arrhythmia is stored such that a history of the incidence of dual arrhythmia episodes is available for clinical or therapy evaluation. According to the present invention, dual arrhythmia incidence is preferably segregated by episodes with recent onset AT/AF and episodes with sustained AT/AF.

Figure 4:
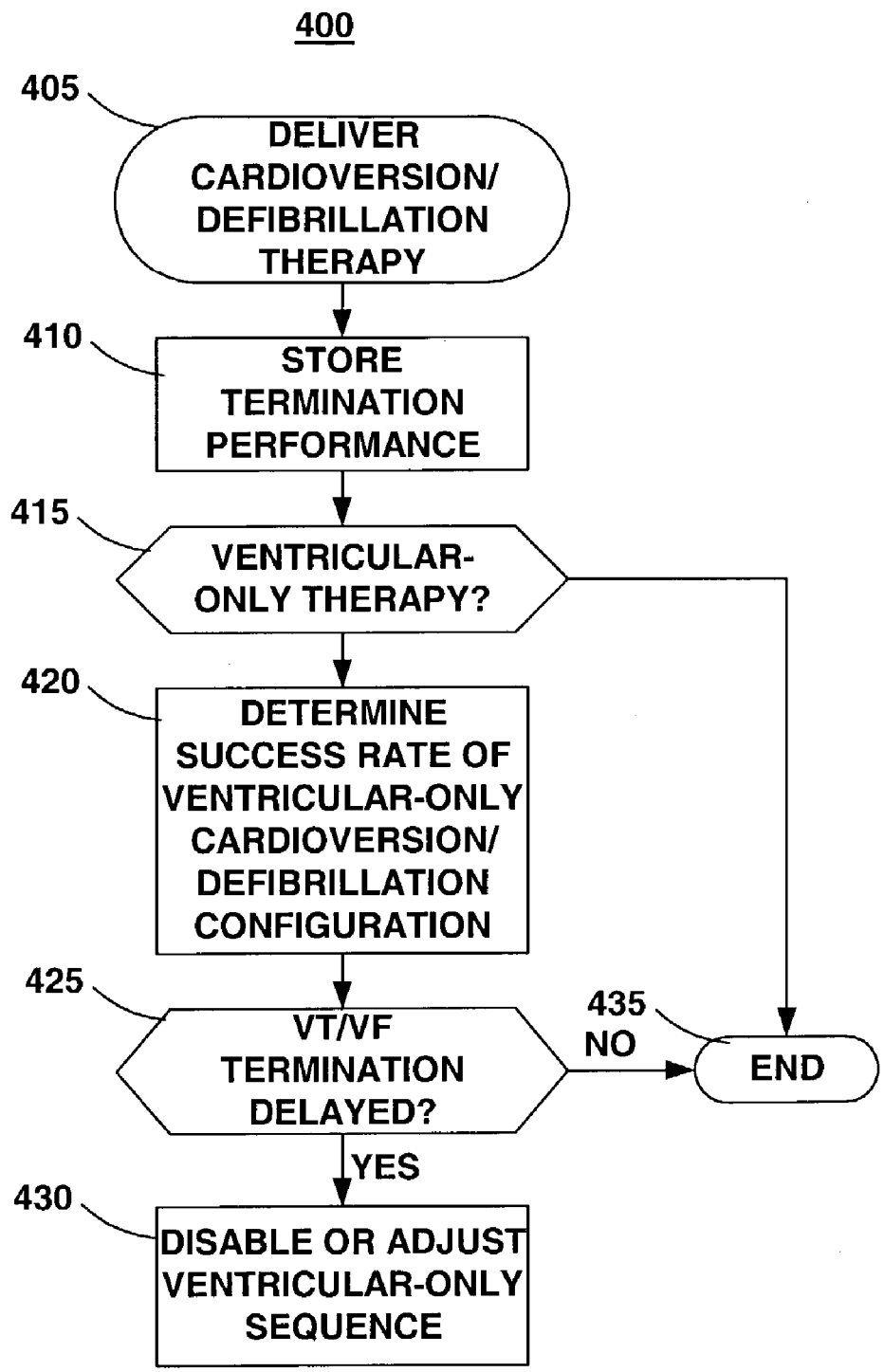
FIG. 4 is a flow chart summarizing steps included in a method for evaluating the performance of a ventricular-only cardioversion/defibrillation configuration.

FIG. 4 is a flow chart of a method for evaluating the performance of a ventricular-only cardioversion/defibrillation configuration, according to the present invention. As illustrated in FIGS. 3 and 4, once either of the default ventricular cardioversion/defibrillation therapy, step 380, the ventricular only cardioversion/defibrillation therapy, step 395, or the dual chamber cardioversion/defibrillation therapy, step 390, is delivered at step 405, the corresponding resulting arrhythmia termination performance is stored by the ICD, step 410. Performance can be stored according to the therapies delivered and the outcome for each therapy. In particular, the ICD may monitor the success of the ventricular-only shock therapies to determine whether delays in terminating ventricular arrhythmias occur as the result of applying ventricular-only therapies.

As such, at decision step 415, a determination is made as to whether a ventricular-only shock sequence was delivered at step 405 in response to the detecting of a dual arrhythmia with sustained AT/AF. If other shock sequences were delivered, method 400 is terminated at step 435. If a ventricular-only shock sequence was delivered, the success rate of the ventricular-only shock sequence in terminating VT/VF is determined at step 420. The success rate may be expressed as the percentage of delivered shocks that resulted in successful termination. The success rate for each shock in a ventricular-only shock sequence may be determined.

A determination is made at step 425 as to whether VT/VF termination is delayed due to delivery of the ventricular-only shock sequence. For example, a success rate for termination on the first shock of a ventricular-only shock sequence that is less than a predetermined percentage may be used to indicate that VT/VF termination is being delayed by attempting to treat only the ventricles. If the VT/VF termination success rate using the ventricular-only shock sequence is acceptable, as determined at decision step 425, no adjustments to the ventricular-only shock sequence are made, and method 400 is concluded at step 435.

However, if it is determined that successful VT/VF termination is being delayed, as determined at decision step 425, the ventricular-only shock sequence is abandoned at step 430 by disabling the ventricular-only shock sequence. The default ventricular shock sequence may be selected upon future VT/VF detections, independent of the existence of sustained AT/AF. The delay to successful VT/VF therapy is not justified by avoiding conversion of AT/AF.

In an alternative embodiment, if the termination performance of the first shock of a ventricular-only shock sequence is unacceptably low, but the termination success rate of a subsequent shock in the ventricular-only shock sequence is acceptable, as determined at decision step 425, the ventricular-only shock sequence may be automatically adjusted at step 430 such that the first shock configuration is reset to be equivalent to the subsequent, more successful, shock configuration.

Some of the techniques described above may be embodied as a computer-readable medium comprising instructions for a programmable processor such as microprocessor 224 or pacer timing/control circuitry 212 shown in FIG. 2. The programmable processor may include one or more individual processors, which may act independently or in concert. A "computer-readable medium" includes but is not limited to read-only memory, Flash memory and a magnetic or optical storage medium. The medium includes instructions for causing a processor to perform the method for configuring delivery of a cardioversion/defibrillation therapy according to the present invention, as described above.

Thus, a system and method have been described for selecting cardioversion/defibrillation shock parameters based on the arrhythmia status of both the atria and the ventricles. Configuring a shock therapy to perform dual chamber cardioversion/defibrillation in the presence of recent-onset AT/AF opportunistically treats both chambers with a single shock. Configuring a shock therapy to perform "ventricular only" cardioversion/defibrillation in the presence of sustained AT/AF reduces the risk of stroke due to thrombus dislodgement from the atria. Furthermore, from a patient monitoring standpoint, the incidence of dual tachycardias can be segregated according to recent onset and sustained AT/AF, which may be of interest to researchers and clinicians in understanding the genesis of these arrhythmias and their treatment. While the present invention has been described according to specific embodiments presented herein, these embodiments are intended to be exemplary, not limiting, with regard to the following claims.

I claim:

1. An implantable medical device, comprising:
    a plurality of electrodes sensing cardiac signals within a plurality of chambers of a heart; and
    control circuitry determining cardiac events in response to the sensed cardiac signals, and delivering a therapy via selected ones of the plurality of electrodes for a first determined cardiac event in response to presence of a second cardiac event, wherein the control circuitry determines, in response to the sensed cardiac signals corresponding to the second cardiac event, whether the second cardiac event is either one of a sustained cardiac event and a recent-onset cardiac event, and selects one of a first shock therapy comprising a defibrillation configuration delivered for simultaneously treating the first cardiac event and the second cardiac event in response to the second cardiac event being a recent-onset cardiac event and a second shock therapy comprising a defibrillation configuration delivered for treating only the first cardiac event and not the second cardiac event in response to the second cardiac event being a sustained cardiac event.

2. The device of claim 1, wherein the first cardiac event corresponds to one of a ventricular tachycardia and a ventricular fibrillation, and the second event corresponds to one of atrial tachycardia and atrial fibrillation.

3. The device of claim 1, wherein the control circuitry determines a time duration of the second cardiac event, and determines that the second cardiac event is a sustained cardiac event in response to the determined time duration being greater than a predetermined time period.

4. The device of claim 3, wherein the predetermined time period is approximately 24 hours.

5. The device of claim 1, wherein the first shock therapy configuration is delivered to treat more than one chamber of the heart and the second therapy is delivered to treat only a single chamber of the heart.

6. The device of claim 5, wherein the more than one chamber corresponds to a ventricle and an atrium of the heart and the single chamber corresponds to a ventricle of the heart.

7. The device of claim 1, wherein the control circuit selects parameters associated with the first shock therapy configuration, including parameters associated with simultaneously terminating both the first cardiac event and the second cardiac event, in response to the determined cardiac events and delivers a single shock according to the parameters associated with simultaneously terminating both the first cardiac event and the second cardiac event.

8. The device of claim 7, wherein the parameters include one or more of a shock vector, a shock energy, a tilt, a waveform, and a waveshape.

9. The device of claim 1, wherein the control circuitry monitors success of the second shock therapy configuration in terminating the first cardiac event, determines whether termination of the first cardiac event is delayed as a result of delivery of the second shock therapy configuration, and selects a third shock therapy configuration in response to the termination of the first cardiac event being delayed.

10. The device of claim 1, wherein the control circuitry determines whether the first cardiac event has terminated, adjusts the second shock therapy configuration and delivers the single shock according to the adjusted second shock therapy configuration in response to the first cardiac event not being terminated, monitors success of the second shock therapy configuration and the adjusted second shock therapy configuration in terminating the first cardiac event to determine whether the second shock therapy configuration and the adjusted second shock therapy configuration are acceptable, and adjusts the second shock therapy configuration to correspond to the adjusted second shock therapy configuration in response to the second shock therapy configuration being unacceptable and the adjusted second shock therapy configuration being acceptable.

11. A method of controlling delivery of therapy in an implantable medical device, comprising:
    sensing cardiac signals;
    determining whether sensed cardiac signals correspond to a first cardiac event and a second cardiac event,
    determining, in response to the sensed cardiac signals corresponding to the first cardiac event and the second cardiac event, whether the second cardiac event is either one of a sustained cardiac event and a recent-onset cardiac event, and
    selecting one of a first shock therapy comprising a first defibrillation configuration corresponding to simultaneously treating the first cardiac event and the second cardiac event in response to the second cardiac event being a recent-onset cardiac event and a second shock therapy comprising a second defibrillation configuration corresponding to treating only the first cardiac event and not the second cardiac event in response to the second cardiac event being a sustained cardiac event.

12. The method of claim 11, wherein the first cardiac event corresponds to one of a ventricular tachycardia and a ventricular fibrillation, and the second cardiac event corresponds to one of atrial tachycardia and atrial fibrillation.

13. The method of claim 11, wherein determining whether the second cardiac event is either one of a sustained cardiac event and a recent-onset cardiac event includes determining a time duration of the second cardiac event and determining the second cardiac event is a sustained cardiac event in response to the determined time duration being greater than a predetermined time period.

14. The method of claim 11, wherein the predetermined time period is approximately 24 hours.

15. The method of claim 11, wherein the first shock therapy configuration is delivered to treat more than one chamber of the heart and the second shock therapy configuration is delivered to treat only a single chamber of the heart.

16. The method of claim 15, wherein the more than one chamber corresponds to a ventricle and an atrium of the heart and the single chamber corresponds to a ventricle of the heart.

17. The method of claim 11 wherein selecting one of the first shock therapy configuration and the second shock therapy configuration includes selecting therapy delivery parameters and wherein selecting the first shock therapy configuration includes selecting therapy delivery parameters associated with delivering a single shock for simultaneously terminating both the first cardiac event and the second cardiac event.

18. The method of claim 17, wherein the therapy delivery parameters include one or more of a shock vector, a shock energy, a tilt, a waveform, and a waveshape.

19. The method of claim 11, further including monitoring success of the second shock therapy configuration in terminating the first cardiac event, determining whether termination of the first cardiac event is delayed as a result of delivery of the second shock therapy configuration, and delivering a third shock therapy configuration in response to the termination of the first cardiac event being delayed.

20. The method of claim 11, further including determining whether the first cardiac event has terminated, adjusting the second shock therapy configuration and delivering the adjusted second shock therapy configuration in response to the first cardiac event not being terminated, monitoring the success of the second shock therapy configuration and the adjusted second shock therapy configuration in terminating the first cardiac event to determine whether the second shock therapy configuration and the adjusted second shock therapy configuration are acceptable, and adjusting the second shock therapy configuration to correspond to the adjusted second shock therapy configuration in response to the second shock therapy configuration being unacceptable and the adjusted second shock therapy configuration being acceptable.

21. A computer readable medium having computer-executable instructions for performing a method comprising:
sensing cardiac signals;
determining whether sensed cardiac signals correspond to a first cardiac event and a second cardiac event,
determining, in response to the sensed cardiac signals corresponding to the first cardiac event and the second cardiac event, whether the second cardiac event is either one of a sustained cardiac event and a recent-onset cardiac event, and
selecting one of a first shock therapy comprising a defibrillation configuration corresponding to simultaneously treating the first cardiac event and the second cardiac event in response to the second cardiac event being a recent-onset cardiac event and a second shock therapy comprising a defibrillation configuration corresponding to treating only the first cardiac event and not the second cardiac event in response to the second cardiac event being a sustained cardiac event.

22. An implantable medical device, comprising:
a plurality of electrodes sensing cardiac signals within a plurality of chambers of a heart; and
control circuitry determining cardiac events in response to the sensed cardiac signals, and delivering a shock therapy via selected ones of the plurality of electrodes for a first determined cardiac event in response to presence of a second cardiac event;
wherein the first cardiac event corresponds to ventricular fibrillation and the second cardiac event corresponds to one of atrial tachycardia and atrial fibrillation;
wherein the control circuitry determines, in response to the sensed cardiac signals corresponding to the second cardiac event, whether the second cardiac event is either one of a sustained cardiac event and a recent-onset cardiac event, and selects one of a first shock therapy comprising a defibrillation configuration corresponding to simultaneously treating the first cardiac event and the second cardiac event in response to the second cardiac event being a recent-onset cardiac event and a second shock therapy comprising a defibrillation configuration corresponding to treating only the first cardiac event and not the second cardiac event in response to the second cardiac event being a sustained cardiac event;
wherein the first shock therapy configuration comprises a single shock therapy configured to simultaneously terminate the first cardiac event and the second cardiac event and the second shock therapy configuration comprises a single shock therapy configured to terminate only the first cardiac event without terminating the second cardiac event.

* * * * *